US008496865B2

(12) United States Patent
Wang et al.

(10) Patent No.: US 8,496,865 B2

(45) Date of Patent: Jul. 30, 2013

(54) METHOD TO MINIMIZE CHAIN SCISSION AND MONOMER GENERATION IN PROCESSING OF POLY(L-LACTIDE) STENT

(75) Inventors: Yunbing Wang, Sunnyvale, CA (US); James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 244 days.

(21) Appl. No.: 12/905,918

(22) Filed: Oct. 15, 2010

(65) Prior Publication Data

US 2012/0091633 A1 Apr. 19, 2012

(51) Int. Cl.
*A61F 2/82* (2006.01)

(52) U.S. Cl.
USPC ............ 264/470; 264/485; 623/1.1; 623/1.38

(58) Field of Classification Search
USPC ........................... 264/485, 470; 623/1.38, 1.1
See application file for complete search history.

(56) References Cited

U.S. PATENT DOCUMENTS 5,085,629 A * 2/1992 Goldberg et al. ................. 604/8
5,868,781 A 2/1999 Killion
6,114,653 A 9/2000 Gustafson
6,131,266 A 10/2000 Saunders
6,612,012 B2 9/2003 Mitelberg et al.
6,865,810 B2 3/2005 Stinson
7,540,997 B2 6/2009 Stinson
2003/0216804 A1 11/2003 DeBeer et al.
2004/0167610 A1 8/2004 Fleming
2005/0119720 A1 6/2005 Gale et al.
2005/0131522 A1 6/2005 Stinson et al.
2006/0111771 A1 5/2006 Ton et al.
2006/0241739 A1 10/2006 Besselink et al.
2007/0142903 A1 6/2007 Dave
2009/0319031 A1 12/2009 Wang et al.
2010/0198331 A1 * 8/2010 Rapoza et al. ............... 623/1.15

FOREIGN PATENT DOCUMENTS

WO WO 2007/142736 12/2007
WO WO 2010/019478 2/2010

OTHER PUBLICATIONS

International Search Report for PCT/US2011/055792, mailed Feb. 7, 2012, 12 pgs.

* cited by examiner

*Primary Examiner* — Galen Hauth

(74) *Attorney, Agent, or Firm* — Squire Sanders (US) LLP

(57) ABSTRACT

Methods of fabricating an implantable medical devices such as stents made from biodegradable polymers are disclosed that reduce or minimize chain scission and monomer generation during processing steps. The method includes processing a poly(L-lactide) resin having an number average molecular weight between 150 to 200 kD in an extruder in a molten state. A poly(L-lactide) tube is formed from the processed resin and a stent is fabricated from the tube. The number average molecular weight of the poly(L-lactide) of the stent after sterilization is 70 to 100 kD.

8 Claims, 2 Drawing Sheets

100

107

105

110

METHOD TO MINIMIZE CHAIN SCISSION AND MONOMER GENERATION IN PROCESSING OF POLY(L-LACTIDE) STENT

BACKGROUND OF THE INVENTION

1. Field of the Invention

This invention relates to fabricating implantable medical devices, such as stents or stent scaffoldings, made from polymers such as poly(L-lactide).

2. Description of the State of the Art

This invention relates to various kinds of implantable medical devices including structures made from polymers. Such implantable medical devices include, but are not limited to, radially expandable prostheses, such as stents and stent grafts, catheters, and pacemaker leads.

Radially expandable endoprostheses are adapted to be implanted in a bodily lumen. An “endoprosthesis” refers to an artificial device that is placed inside the body. A “lumen” refers to a cavity of a tubular organ such as a blood vessel. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. “Stenosis” refers to a narrowing or constriction of the diameter of a bodily passage or orifice. In such treatments, stents reinforce body vessels and prevent restenosis following angioplasty in the vascular system. “Restenosis” refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. “Delivery” refers to introducing and transporting the stent through a bodily lumen to a region, such as a lesion, in a vessel that requires treatment.

“Deployment” corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of requirements such as the radial strength necessary to withstand the structural loads, namely radial compressive forces, imposed on the stent as it supports the walls of a vessel. Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for implantable medical devices, such as stents, to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable bioabsorbable polymers can be configured to partially or completely erode away after the clinical need for them has ended.

SUMMARY OF THE INVENTION

Various embodiments of the present invention include a method of making a stent comprising: providing PLLA resin having an Mn between 150 to 200 kD; processing the PLLA resin in an extruder in a molten state; forming a PLLA tube from the processed PLLA resin; and fabricating a stent from the PLLA tube.

Further embodiments of a method of making a stent comprise: providing PLLA resin; processing the PLLA resin in an extruder in a molten state at a temperature in the extruder is 195° C. to 210° C.; forming a PLLA tube from the processed PLLA resin; fabricating a stent scaffolding from the PLLA tube; and sterilizing the stent scaffolding through exposure to e-beam radiation at a dose of 20-35 kGy, wherein the Mn of the sterilized stent scaffolding is at least 70 kD.

Additional embodiments of the present invention include a method of making a stent comprising: providing PLLA resin having a Mn of 150-200 kD; processing the PLLA resin in an extruder in a molten state; forming a PLLA tube from the processed PLLA resin; fabricating a stent scaffolding from the PLLA tube; and sterilizing the stent scaffolding through exposure to e-beam radiation at a dose of 20-35 kGy, wherein the Mn of the scaffolding prior to sterilization is 100 to 150 kD, and wherein the Mn of the sterilized stent scaffolding is at least 70 kD.

Other embodiments of the present invention include a method of making a stent comprising: providing PLLA resin; processing the PLLA resin in an extruder in a molten state; forming a PLLA tube from the processed PLLA resin; fabricating a stent scaffolding from the PLLA tube; and sterilizing the stent scaffolding through exposure to e-beam radiation at a dose of 22-27 kGy, wherein a % change in Mn of the PLLA resin prior to processing in the extruder to after sterilization is less than 70%, wherein the % change is defined as Mn (the PLLA resin prior to processing in the extruder)−Mn (the PLLA scaffolding after sterilization)]/Mn (the PLLA resin prior to processing in the extruder).

DETAILED DESCRIPTION OF THE INVENTION

Embodiments of the present invention relate to methods of fabricating implantable medical devices such as stents made from biodegradable polymers. In such embodiments, the methods are directed to reducing or minimizing chain scission and monomer generation during processing steps. Embodiments are also directed to a stent fabricated from these methods. The stents have a reduced concentration of low molecular weight species and monomers which are byproducts of thermal and radiation processing steps. The methods and devices described herein are generally applicable to any implantable medical device. In particular, the methods can be applied to tubular implantable medical devices such as self-expandable stents, balloon-expandable stents, stent-grafts, and pacemaker leads.

The embodiments are particularly relevant, for reasons discussed below, to implantable medical devices, such as stents, having a polymeric substrate or scaffolding, a polymer-based coating, a drug-delivery coating, or a combination thereof. The fabrication methods are further directed to fabrication of stent scaffoldings are the part of the stent structure which, on their, own, provide patency to a lumen when the scaffolding is expanded within a vessel.

Figure 1:
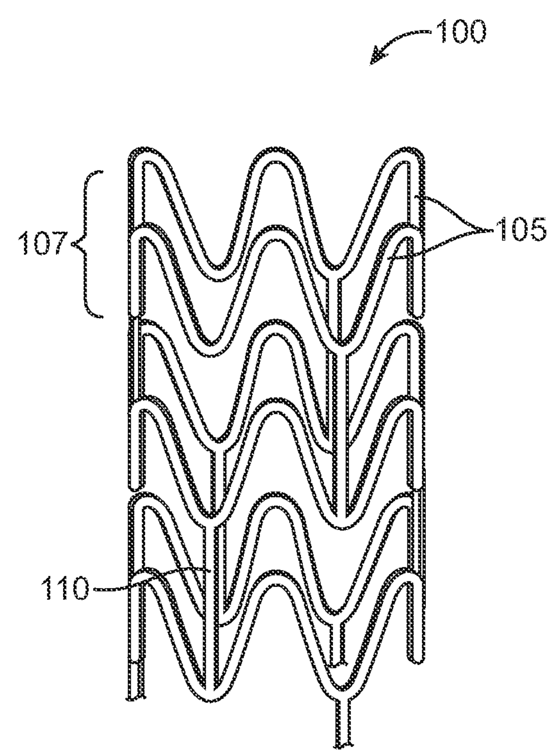
FIG. 1 depicts a stent.

FIG. 1 depicts a view of an exemplary stent 100. In some embodiments, a stent may include a body, backbone, or scaffolding having a pattern or network of interconnecting structural elements 105. Stent 100 may be formed from a tube (not shown). FIG. 1 illustrates features that are typical to many stent patterns including cylindrical rings 107 connected by linking elements 110. As mentioned above, the cylindrical rings are load bearing in that they provide radially directed force to support the walls of a vessel. The linking elements generally function to hold the cylindrical rings together. A stent scaffolding such as stent 100 may be fabricated from a tube by forming a pattern in the tube with a technique such as laser cutting or chemical etching.

In some embodiments, the diameter of the polymer tube prior to fabrication of a stent may be between about 0.2 mm and about 5.0 mm, or more narrowly between about 1 mm and about 4 mm. An exemplary tube diameter of the tube that is laser cut to form the stent scaffolding is 3 to 4 mm. The wall thickness a tube formed by extrusion or injection molding may be 0.05-2 mm, 0.05-1.05 mm, or 0.08-1.02 mm.

Furthermore, stents and other implantable medical devices have been designed for the localized delivery of a therapeutic agent. A medicated stent may be constructed by coating the device or substrate with a coating material containing a therapeutic agent. The underlying scaffolding or substrate of the device may also contain a therapeutic agent.

In embodiments of the present invention, an implantable medical device can be made partially or completely from a biodegradable, bioabsorbable, bioresorbable, or biostable polymer. A polymer for use in fabricating an implantable medical device can be biostable, bioabsorbable, bioresorbable, biodegradable, or bioerodable. Biostable refers to polymers that are not biodegradable. The terms biodegradable, bioabsorbable, bioresorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes. In some treatment situations, a degradation time of less than 2 years may be desirable, for example, between 6 and 14 months, or more narrowly, between 8 and 12 months. Degradation time refers to the time for complete erosion of a device from an implant site or in vitro.

The present invention is particularly applicable to poly(L-lactide) (PLLA) and poly(DL-lactic acid) (PDLA). The present invention is generally applicable to bioresorbable aliphatic polyesters such as polyglycolide (PGA), polycaprolactone (PCL), and copolymers thereof and with PLLA and PDLA, such as poly(glycolide-co-lactide) (PLGA), poly(L-lactide-co-caprolactone), and poly(L-lactide-co-DL-lactide). In general, the present invention is applicable to any bioresorbable polyester made by ring-opening polymerization. A stent scaffolding can be made of 100% of one or a combination of the above polymers. Additionally, the scaffolding can also be drug-free.

The molecular weight of polymer of the final or finished stent product is very important for proper functioning or treatment by the stent. Final or finished product can refer to the stent or stent scaffolding right after sterilization, any time after sterilization, or right before delivery in a human patient. The importance of the molecular weight stems from the dependence of properties and behavior of the stent in the body on molecular weight, most notably, mechanical properties and degradation properties.

Both the magnitude of the strength and modulus or stiffness of the polymer depend on molecular weight, being inversely proportional to molecular weight. The stent property of radial strength depends on these material properties. "Radial strength" of a stent can be defined generally as the inward radial pressure at which a stent experiences irrecoverable deformation. The ability of the stent to resist periodic inward pressure, for example imposed by vessel walls, is directly related to the polymer modulus. For successful treatment, the stent must at least initially have sufficient radial strength and stiffness to maintain patency of a lumen at a increased diameter, that is, support a lumen at a given diameter.

Additionally, the time dependence of mechanical properties and stent properties is also significant and dependent on the molecular weight. The stent must be able to support the lumen at the increased diameter for a sufficiently long enough time period to allow the vessel walls to remodel and remain at the increased diameter without support. As the polymer degrades, molecular weight decreases and the strength and modulus decrease along with the radial strength and radial stiffness of the stent. After a critical time period the radial strength of the stent decreases to the point that it can no longer support the lumen (due to the decrease in molecular weight which causes a decrease in strength and stiffness). Eventually, at another later critical time period after implantation, the stent loses structural integrity, i.e., breaks apart. At still another even later critical time period after implantation, the stent completely resorbs away from the treatment site. These critical times periods each are inversely proportional to the molecular weight of the finished stent product. Thus, the molecular weight of the finished product must be sufficiently high so that these critical times are high enough for successful treatment. In particular, the finished product must have a molecular weight high enough so that the stent maintains radial strength a time long enough to achieve remodeling sufficient for the lumen walls to be maintained at a desired diameter.

The minimum target molecular weight (Mn) for a coronary stent made of PLLA with parameters described below is an Mn between 60-110 kD, 60 and 100 kD, 60-90 kD, 70-80. An exemplary stent is made of struts having a cross-section with thickness and width of 140-160 microns, or more narrowly, 150 microns. The crystallinity of the PLLA stent is 30-55%, or more narrowly, 40-50%.

The fabrication of a polymer implantable medical device, such as a bioresorbable polymer stent scaffolding, can include several processing steps. These steps include forming a polymeric construct, such as a tube, by melt processing; forming a stent body or scaffolding from the tube by laser machining a stent pattern in the tube; and radiation sterilization of the stent. Melt processing can include extrusion or injection molding. Additional steps can include radially deforming the tube formed from extrusion to increase radial strength, application of a therapeutic coating on the stent body; and crimping the stent over a catheter or delivery balloon.

The polymer during the melt processing, such as extrusion, is free or substantially free of a solvent, such as an organic solvent. Substantially free is less than 0.1%, 0.01%, or less than 0.001% of solvent as compared to the polymer. Thus, extrusion, as used herein, is distinguished from techniques such as gel extrusion or solvent extrusion which are known to a person of ordinary skill in the art of polymer processing. In these methods, a mixture of a polymer and solvent is conveyed through an extruder and a construct is formed there from, followed by removal of all or most of the solvent.

In general, polymers, such as biodegradable and aliphatic polyesters, are subject to chemical degradation during processing. Chemical degradation results in a decrease in molecular weight of polymer due to chemical reactions between polymer chains or other species and polymer chains. The chemical reactions, thus, can result in the reduction or degradation in molecular weight of the polymer. The chemical degradation can be due to exposure to high temperature, high forces (e.g., shear forces) or due to exposure to radiation. Melt processing and radiation sterilization, in particular, cause a significant drop in molecular weight of the polymer during stent fabrication. The decrease in molecular weight can adversely effect mechanical properties and other properties of the polymer such as degradation behavior and drug release properties.

The chemical degradation of polymers can arise from several different chemical reaction mechanisms. For example, heat and radiation cause chain scission by free radical reactions and non-free radical reactions. Oxygen can accelerate the free radical reactions. Free radical formation results in chain scission, resulting in the formation of a series of byproducts, such as monomers (e.g., lactide monomers from PLLA), cyclic oligomers, and shorter polymer chains. Essentially, chain scission generates new species (byproducts) with unknown or uncharacterized endgroups. Both melt processing and radiation sterilization result in the formation of low molecular weight species which are present in the final product.

Poly(L-lacide), for example, has hydroxyl end groups and has the general formula: H-[OCH(CH3)CO]n-OH, which will be abbreviated as: PLLA-OH. Poly(L-lactide) is subject to thermal degradation at elevated temperatures, with significant degradation (measured as weight loss) starting at about 200° C. and increasing at higher temperatures. The polymer is subject to chemical degradation by both free radical and non-free radical mechanisms that result in random chain scission that generates byproducts such as oligomers and lactide monomers. To explain the presence of lactide at higher temperatures, it has been postulated that there is an equilibrium between the lactide monomer and the polymer chain. In addition to lactide, the degradation products also include aldehydes, and other cyclic oligomers.

The effect of stent processing (extrusion, laser machining, and radiation sterilization) on properties of PLLA has been observed. The resorption time of the stent is lower than the resin material that is fed to the extrusion process. For example, a PLLA resin not subjected to melt processing typically has a reported resorption times of 2 years (Medical Device Manufacturing & Technology 2005) and 3 years (The Biomedical Engineering Handbook, Joseph D. Bronzino, Ed. CRC Press in Cooperation with IEEE Press, Boca Raton, Fla., 1995). An e-beam sterilized PLLA stent can have a resorption time of 18 months to two years. Lancet.com Vol. 373 Mar. 14, 2009, incorporated herein by reference.

In melt processing such as in extrusion, the degree of chemical degradation and, thus loss of molecular weight, is inversely proportional to the extrusion temperature. A polymer tube can be formed through melt processing methods such as extrusion or injection molding. In extrusion, a polymer melt is conveyed through an extruder barrel to an exit port. The polymer resin is fed to an extruder barrel near its proximal end as a melt or in a solid form, for example, as a pellet from a hopper. The polymer in the extruder barrel is heated to temperatures near or above the melting temperature (Tm) of the polymer and exposed to shear forces and pressures that are generally far above ambient by a rotating extruder screw. Table 1 provides melting temperatures reported for several polymers. The polymer melt exits the distal end of the extruder barrel into a die. The die imparts a cylindrical shape to the polymer melt exiting the die, which is cooled to form a tube. Representative examples of extruders for use with the present invention may include single screw extruders, intermeshing co-rotating and counter-rotating twin-screw extruders, and other multiple screw masticating extruders.

The polymer cannot be conveyed through the extruder barrel unless the viscosity is sufficiently low. The viscosity of a polymer melt is known to be inversely proportional to the molecular weight. Thus, the higher the starting molecular weight of the resin, the higher the extrusion temperature required to provide a viscosity low enough for processing.

Exemplary processing of PLLA resin can be performed with a ¾" single screw extruder. For a resin with a Mn of about 200 kD, the processing temperature is 200-210° C. and the residence time is 8-10 min. The tube is quenched in a room temperature water bath as it exits the die. The extruder barrel pressure is about 2000 psi. The post-extrusion degree of crystallinity is about 10%-15%.

TABLE 1

Melting temperatures and glass transition temperatures of exemplary polymers.

| Polymer | Melting Point (° C.)[1] | Glass Transition Temp (° C.)[1] |
|---|---|---|
| PGA | 225-230[1] | 35-40 |
| PLLA | 173-178[1] | 60-65 |
| PCL | 58-63[1]<br>60[2] | (−65)-(−60) |
| PDO | N/A | (−10)-0 |

[1]Medical Plastics and Biomaterials Magazine, March 1998.
[2]Science, Vol. 297 p. 803 (2002)

Typically, a stent is sterilized after crimping and packaging the crimped stent. Irradiation, either gamma radiation or electron beam (e-beam) radiation, are typically used for terminal sterilization of medical devices. Radiation sterilization also causes chemical degradation to the polymer in a stent. High-energy radiation, such as electron beams (e-beam) and gamma radiation, tends to produce ionization and excitation in polymer molecules. These energy-rich species undergo dissociation, subtraction, and addition reactions in a sequence leading to chemical stability. The stabilization process can occur during, immediately after, or even days, weeks, or months after exposure to radiation which often results in physical and chemical cross-linking or chain scission.

The significant drops (discussed below) in molecular weight caused by extrusion and radiation sterilization provide suggest that the molecular weight of the PLLA resin fed to an extruder should have a molecular weight (Mn) as high as possible. Selecting a high molecular weight should be the best approach to provide a final product molecular weight high enough to maintain radial strength for the requisite time period treatment and to address safety concerns.

As an example, the inventors selected a PLLA resin with relatively high initial Mn of 360 kD for the tubing extrusion process. A processing temperature of about 225-235° C. is required to sufficiently reduce the viscosity for processing the polymer melt. When such high molecular weight resin is used for extrusion, it is difficult to melt uniformly and the viscosity is very high even at the high processing temperature. The polymer melt is also subjected to high shear force, and pressure, and with relatively long residence time up to 15 min. Such processing conditions caused significant chain scission and produced significant thermal breakdown by-products, and potentially favor the monomer generation. The molecular weight dropped from 360 to about 250 kD after extrusion, while the maximum monomer content generated was up to 4%. After e-beam exposure of 25 kGy, the Mn dropped from about 250 kD to about 85 kD, which is an acceptable molecular weight for treatment. However, as discussed below even though this scheme produces a finished good molecular weight in an acceptable range, it results in a product with a high concentration of degradation byproducts, which inventors have found adversely effects resorption of the polymer in vivo, i.e., the resorption rate is increased by the byproducts. This sometimes dramatically decreases the time the radial strength is maintained at a level that lumen walls can be supported.

Therefore, as summary of the problem with this approach is as follows. It appears reasonable to select a resin with molecular weight as high as possible to obtain a final molecular weight that is sufficiently high. However, the higher the molecular weight, the higher the extrusion temperature required to lower the viscosity. The disadvantage of this is that the higher temperature increases the amount of unfavorable degradation byproducts.

Although use of a high molecular weight starting material can provide a stent with acceptable properties for safe treatment, the present invention represents an improvement over this method for reasons discussed below. Embodiments of the present invention are based on the realization by the inventors that the degradation behavior depends on factors in addition to the molecular weight of the final product. Specifically, the degradation byproducts generated by melt processing and radiation significantly increases the degradation rate, increasing the rate that radial strength deteriorates upon implantation. Therefore, the time that a stent can maintain support of a lumen decreases with more byproducts. These byproducts include low molecular weight oligomers and monomers.

Therefore, selecting a resin molecular weight as high as possible that requires a high melt processing temperature that results in more byproducts that are adverse to the stent properties. To the inventors' knowledge, prior to this realization of the link between such byproducts and stent properties, it has not been recognized that thermal degradation byproducts can significantly compromise the degradation properties of a polymer stent, in particular, the time that a stent can support a lumen.

Embodiments of the present invention include selecting the molecular weight of the polymer resin, for example PLLA, in a manner that is contrary to the approach outlined above of selecting the molecular weight as high as possible. In the embodiments of the present invention, a lower molecular weight resin is selected which then allows a lower processing temperature. This lower processing temperature necessarily results in less harmful byproducts as compared to the approach discussed above.

In some embodiments, a relatively low melt processing temperature is selected and a molecular weight of the resin is selected that it has a viscosity at the temperature that is low enough for extrusion. In some embodiments, the selected molecular weight may be the highest molecular weight that can be processed at the selected temperature. In other words, a resin with a molecular weight higher than the selected molecular weight would have a viscosity too high to process at the selected temperature. In the case of PLLA, the selected temperature may be 20-30° C. higher than the Tm and Mn of the resin is 150-200 kD.

The inventors have further recognized the use of a lower molecular weight resin (150-200 kD) can provide a finished stent molecular weight that is the same or slightly lower than the use of a higher molecular weight resin (250-350, 350-400, 400 or higher). This is the case even with an initial resin molecular weight that is significantly lower, for example, less than 50% of a higher molecular weight resin.

This recognition is based on data showing that the degree of chain scission from e-beam exposure on PLLA is inversely proportional with the molecular weight pre-exposure. In other words, the degree of chain scission decreases with increasing molecular weight.

Figure 2:
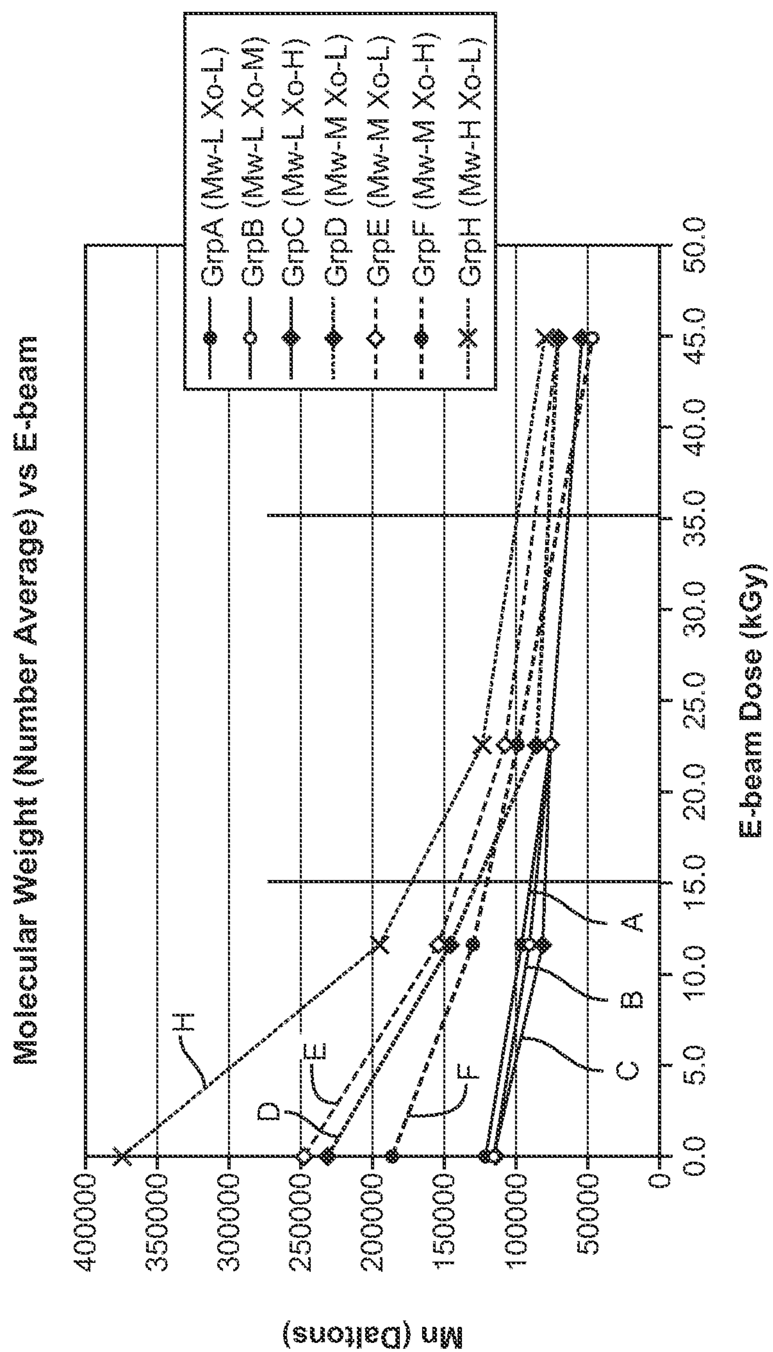
FIG. 2 depicts the number average molecular weight as a function of e-beam dose for samples of poly(L-lactide) resin with different initial number average molecular weights.

FIG. 2 depicts the Mn as a function of e-beam dose for samples of PLLA resin with different initial Mn. Sample preparation and sterilization are given below in the section labeled Example of this application. The sample details are provided in Table 2. As shown in the table, the samples are categorized by three crystallinity groups and three molecular weight groups.

TABLE 2

Number Average MW (Mn) of Disk Samples (Dose = 0 kGy)

| | | Number Average MW-Mn (kDa) | | |
|---|---|---|---|---|
| | | Low | Medium | High |
| Crystallinity | Low (15%)* | Group A 122 | Group D 231 | Group G N/A |
| | Medium (35%)* | Group B 114 | Group E 247 | Group H 375 |
| | High (55%)* | Group C 116 | Group F 185 | Group I N/A |

As shown in FIG. 2, the change in Mn with e-beam dose is very sensitive to initial Mn. The initial high Mn samples, 250 kD and above, experience very high losses with small changes in e-beam dose (e.g., at 25 kGy, Mn of sample H is only about 35% of initial Mn). The initial medium Mn samples are less sensitive to dose but still experience relatively large losses (at 25 kGy Mn of sample F is about 55% of initial Mn). The initial low Mn samples are relatively flat (compared to the other groups) across the range of dose evaluated (0 to 50 kGy). This is especially true within the possible range of sterile doses to be experienced by the stents during radiation sterilization (20 to 35 kGy). Starting with a higher initial Mn provides a higher Mn drop, within the range of e-beam doses that the stent could possibly see (20-35 kGy), than starting with a lower initial Mn. The change in molecular weight with e-beam dose is not effected by initial crystallinity over the range of crystallinity from 5-55% for low and medium initial molecular weight.

It is clear from FIG. 2, that the e-beam process acts as an "equalizer" of sorts between starting with high molecular weigh and lower molecular weight. The change in molecular weight being more significant for high molecular weight materials subjected to e-beam brings the molecular weights for high and low molecular weight starting materials much closer after e-beam exposure.

As noted above, sterilization is typically the final step of the manufacturing process for a stent. The extrusion step accounts for most of the loss in molecular weight just prior to sterilization. Laser machining accounts for another potential loss in molecular weight. Therefore, the sample molecular weights correspond to the molecular weight of the stent after losses due to at least the extrusion and laser machining steps. To determine the molecular weight of a resin that would give the post-radiation exposure molecular weight at a given dose in FIG. 2, the loss in molecular weight from melt processing and laser machining at least would have to be taken into account.

The use of a resin with a certain lower range of Mn has several processing advantages for extrusion. This includes that the resin can be readily melted more uniformly with low viscosity at a lower temperature. Additionally, lower shear force and pressure can be applied with shorter residence time. These factors result in fewer degradation byproducts during extrusion.

Additionally, the use of such lower molecular weight resin in combination with lower processing temperatures will result in a finished good with a significantly lower concentration of degradation byproducts. With respect to the melt processing at lower temperatures, fewer degradation byproducts are generated than processing a higher molecular weight polymer at higher temperatures. The relative decrease in molecular weight during melt processing is expected to be lower than at higher temperatures. For example, an extrusion temperature in the range of 195-210° C. as compared to 225 to 235° C. Therefore, there will be fewer low molecular weight species with various end groups and monomers generated.

Another advantage of using the lower molecular weight resin polymer is that it results in a lower molecular weight polymer just prior to radiation sterilization. The lower molecular weight construct will undergo significantly less chain scission during e-beam exposure (as shown by FIG. 2) than the higher molecular weight construct. Therefore, both the extrusion and e-beam steps will generate fewer degradation byproducts and the finished product will have significantly fewer degradation products than a finished product made from an initial higher molecular weight resin.

As indicated above, these degradation byproducts can significantly compromise the degradation properties of a polymer stent such as the time dependence of mechanical properties. The finished good from the lower molecular weight resin will maintain mechanical properties longer and more consistently than a finished good from the high molecular weight starting material.

The PLLA resin for the various embodiments of the present invention may be obtained commercially. For example, PURAC sells PLLA of various molecular weights under the trade name PURASORB®. These include: PURABSORB® PL 18 (inherent viscosity=1.8 dL/g), PURABSORB® PL 24 (inherent viscosity=2.4 dL/g), PURABSORB® PL 32 (inherent viscosity=3.2 dL/g), and PURABSORB® PL 49 (inherent viscosity=4.9 dL/g).

Certain embodiments of fabricating a stent include providing a PLLA resin. The resin melt is processed in an extruder in a molten state to form a PLLA tube. In some embodiments, the processing temperature in the extruder is less than 210° C., less than 200° C., 195 to 210° C., or 195 to 210° C. A stent scaffolding is made from the polymeric tube by cutting a pattern into the tube, for example, by laser cutting. The polymeric scaffolding is exposed to e-beam radiation for sterilization. The Mn of the scaffolding after sterilization is 70 to 110 kD, or more narrowly, 80-90 kD.

In this and other embodiments, the fabrication of the stent can include additional processing steps including radial expansion of the tube prior to cutting the pattern, coating the scaffolding with a mixture of drug and polymer, and crimping the stent scaffolding over a delivery balloon.

Additional embodiments of fabricating a stent include providing a PLLA resin with an Mn between 150 to 200 kD. The resin is melt processed in an extruder in a molten state to form a PLLA tube with the processing temperature in the extruder being 195 to 210° C., or more narrowly, 195 to 210° C. A stent scaffolding is made from the polymeric tube by cutting a pattern into the tube, for example, by laser cutting. The polymeric scaffolding is exposed to e-beam radiation for sterilization. The Mn of the scaffolding prior to sterilization is 100 to 150 kD, or more narrowly, 110-130 kD. The Mn of the scaffolding after sterilization is 70 to 110 kD, or more narrowly, 80-90 kD.

Further embodiments of fabricating a stent include providing a PLLA resin and melt processing in an extruder in a molten state to form a PLLA tube, making a stent scaffolding from the polymeric tube by cutting a pattern into the tube, for example, by laser cutting, and exposing the polymeric scaffolding to e-beam radiation for sterilization. In some embodiments, the change in Mn from the PLLA resin prior to melt processing to after sterilization (final product) is less than 200%, less than 100%, less than 50%, 50-100%, 100-150%, or 150-200%.

The % change in molecular weight is defined by: 100%×[Mn (resin)−Mn (final product)]/Mn (resin). In other embodiments, the % change in Mn of the stent scaffolding immediately prior to sterilization to after sterilization is less than 40%, 40-60%, or 40-50%, where the % change in Mn is defined similar to above.

The methods of the present invention applies to stent scaffoldings made from other polymers including, but are not limited to, poly(trimethylene carbonate), polydioxanone, poly(hydroxy butyrate), poly(butylene succinate), polyesteramide, poly(hydroxy butyrate-co-hydroxyvalerate), poly(butylene succinate adipate), poly(hydroxyl alkanoates), poly(hydroxyl butyrate), poly(hydroxyl hexanoate), and poly(hydroxyl valerate).

For the purposes of the present invention, the following terms and definitions apply:

The term "molecular weight" can refer to one or more definitions of molecular weight.

"Molecular weight" can refer to the molecular weight of individual segments, blocks, or polymer chains. "Molecular weight" can also refer to weight average molecular weight or number average molecular weight of types of segments, blocks, or polymer chains. The number average molecular weight (Mn) is the common, mean, average of the molecular weights of the individual segments, blocks, or polymer chains. Molecular weight is typical expressed in grams/mole which is referred to as "Daltons." It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "inherent viscosity" (of a polymer) is the ratio of the natural logarithm of the relative viscosity, ηr, to the mass concentration of the polymer, c, i.e. ηinh=(ln ηr)/c, where the relative viscosity (ηr) is the ratio of the viscosity of a polymer solution, η, to the viscosity of the solvent (ηs), ηr=η/ηs.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

EXAMPLE

Sample Preparation

The data for FIG. 2 was generated from test samples that consisted of small disks, or pieces taken from these disks, which were made from PLLA resin supplied by PURAC. The disks were fabricated using a mold and heated press process:

1) A Carver Press was pre-heated to 420° F.

2) Resin was placed into the cavity of the mold, which was sandwiched between aluminum foil to prevent the resin from sticking to the press.

3) The molds were then placed into and held in the Carver Press for 15 minutes.

The medium crystallinity group was also sandwiched and heated between metal plates to retain heat for a longer period of time during the cooling process.

4) Cooling times:

a. Low crystallinity—The disk molds were removed from the press and allowed to cool in the mold for 5 minutes at room temperature before the disks were removed from mold.

b. Medium crystallinity—The disk molds, and metal plates on top and bottom of the molds, were removed from the press and allowed to cool in the sandwich configuration for 50 minutes. The disk molds were then removed from the metal plates and allowed to cool in the mold for 5 minutes at room temperature before the disks were removed from the mold.

c. High crystallinity—After the 15 minute heating period the Carver Press heating element was turned off. The disk molds were left in the press to cool for 24 hours before removing the disks from the molds.

Nine groups of samples were fabricated. Refer to Table 3 for the name, PLLA resin, target crystallinity and quantity of disks created for each group.

TABLE 3

Disk Sample Groups.

| Group Name | PLLA Resin | Crystallinity Target (%) | Quantity of Disks |
|---|---|---|---|
| A | PURABSORB ® PL 18 | 15 | 15 |
| B | PURABSORB ® PL 18 | 35 | 15 |
| C | PURABSORB ® PL 18 | 55 | 15 |
| D | PURABSORB ® PL 32 | 15 | 15 |
| E | PURABSORB ® PL 32 | 35 | 15 |
| F | PURABSORB ® PL 32 | 55 | 15 |
| G | PURABSORB ® PL 49 | 15 | 15 |
| H | PURABSORB ® PL 49 | 35 | 15 |
| I | PURABSORB ® PL 49 | 55 | 15 |

Sterilization

All samples in a given sterilization group (e.g. 12.5 kGy, 25 kGy and 50 kGy) were sterilized at the same time to assure they received the same target dose.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:

providing PLLA resin having a Mn of 150-200 kD;

processing the PLLA resin in an extruder in a molten state;

forming a PLLA tube from the processed PLLA resin;

fabricating a stent scaffolding from the PLLA tube; and sterilizing the stent scaffolding through exposure to e-beam radiation at a dose of 20-35 kGy, wherein the Mn of the scaffolding prior to sterilization is 100 to 150 kD, and wherein the Mn of the sterilized stent scaffolding is at least 70 kD.

2. The method of claim 1, wherein a processing temperature in the extruder is 195° C. to 210° C.

3. The method of claim 1, wherein the dose of the e-beam radiation is 22-27 kGy.

4. A method of making a stent comprising:

providing PLLA resin;

processing the PLLA resin in an extruder in a molten state;

forming a PLLA tube from the processed PLLA resin;

fabricating a stent scaffolding from the PLLA tube; and sterilizing the stent scaffolding through exposure to e-beam radiation at a dose of 22-27 kGy, wherein a % change in Mn of the PLLA resin prior to processing in the extruder to after sterilization is less than 50%, wherein the % change is defined as −Mn (the PLLA resin prior to processing in the extruder)−Mn (the PLLA scaffolding after sterilization)]/Mn (the PLLA resin prior to processing in the extruder).

5. The method of claim 4, wherein a temperature of the PLLA resin in the molten state in the extruder is less than 210° C.

6. The method of claim 1, wherein the Mn of the scaffolding prior to sterilization is 110 to 130 kD.

7. The method of claim 1, wherein the Mn of the sterilized stent scaffolding is between 70 and 110 kD.

8. The method of claim 1, wherein the Mn of the sterilized stent scaffolding is between 80 and 90 kD.

* * * * *